United States Patent

Hoffmann, Jr. et al.

[11] Patent Number: 5,482,705
[45] Date of Patent: Jan. 9, 1996

[54] COLD-WATER (FRESH OR SALT) AND NO-WATER SHAVING LOTION

[76] Inventors: Carl R. Hoffmann, Jr., 7490 Lake Hazel Rd., Boise, Id. 83709; Morton H. Katz, 100 Westview Rd., Spring Valley, N.Y. 10977

[21] Appl. No.: 79,672

[22] Filed: Jun. 18, 1993

[51] Int. Cl.⁶ .................................................. A61K 7/15
[52] U.S. Cl. .................................. 424/73; 424/402
[58] Field of Search ........................... 424/73, 402, 70, 424/114

[56] References Cited

U.S. PATENT DOCUMENTS

| | | | |
|---|---|---|---|
| 4,525,344 | 6/1985 | Tutsky | 424/73 |
| 4,870,010 | 9/1989 | Hayes | 424/114 |
| 4,963,352 | 10/1990 | Roberts | 424/73 |
| 4,994,265 | 2/1991 | White | 424/73 |

*Primary Examiner*—Thurman K. Page
*Assistant Examiner*—William E. Benston, Jr.
*Attorney, Agent, or Firm*—Stoll, Miskin, Previto & Hoffman

[57] ABSTRACT

A shaving preparation in the form of a lotion having a neutral pH and adapted for shaving with cold water (fresh or salt) as well as without water.

1 Claim, No Drawings

COLD-WATER (FRESH OR SALT) AND NO-WATER SHAVING LOTION

BACKGROUND OF THE INVENTION

1. Field of the Invention

Shaving preparations primarily for use by members of the armed forces under field conditions, and by campers, sportsmen and other outdoorsmen and daily use at home and traveling.

2. Description of the Prior Art

The prior art is described in Pat. No. 2,655,480 issued on Oct. 13, 1953 to Joseph G. Spitzer and Irving Reich, and in the case of *Carter Products, Inc. et al.* v. *Colgate-Palmolive Company, et al.*, 130 F.S. 554 (District Court, D. Maryland, 1955) in which that patent was adjudicated.

The prior art includes the so-called "brushless shaving cream" regarding the Court in the *Carter Products* case wrote as follows (130 F.S. at pp. 560, 561):

> The other relatively recent and prevalent preparation to facilitate shaving is the so-called "brushless shaving cream". This forms no lather, but is merely spread on the face like cold cream, to provide a hair-softening medium and a lubricant for the razor blade. Brushless shaving creams are relatively inefficient compared with lather. They are less pleasing to use, harder to remove from the razor and the washbowl, and are in vogue primarily because of greater convenience, since no whipping up of lather is required.

Also included in the prior art is the so-called "moisturizing skin lotion" used on infants and on adults as well. In one case known to applicants, a baby lotion sold by The Mennen Co. of Morristown, N.J. under the trademark "Baby Magic" is represented to be "Perfect as a moisturizing shaving lotion for silky, smooth legs". The formula, as stated on the container of this product is as follows:

Ingredients: Water, Glycerin, Glyceryl, Stearate, Cetyl Alcohol, Mineral Oil, Peg-100 Stearate, Lanolin, Alcohol, Fragrance, Lanolin, Methylparaben, Lapyrium Chloride, Propylparaben Benzalkonium Chloride, D & C Red No. 22, Ext. D & C Violet No. 2.

It has been determined in the laboratory of one of the present applicants that this product has a pH of 3.7.

SUMMARY OF THE INVENTION

This invention is of a shaving lotion that is adapted for use as a cold-water (fresh or salt) shaving lotion when hot water is not available, and as a no-water shaving lotion when neither hot nor cold water (fresh or salt) is available.

In general, baby lotions are left at the formula's inherent pH. In the present invention, the product is buffered to a neutral pH, and this is clearly distinguishable from the 3.7 pH of the Mennen Baby Magic product.

It is applicant's opinion that their formula as herein disclosed, buffered to a neutral pH, distinguishes over the prior art, and provides a very useful shaving lotion that functions without water as well as with cold water (fresh or salt), conditions for which all prior art shaving preparations known to applicants are not suited.

DESCRIPTION OF PREFERRED EMBODIMENTS OF THE INVENTION

The cold-water (fresh or salt) and no-water shaving lotion comprising the present invention is based on the following formula of active ingredients, having a neutral pH:

| Basic formula of active ingredients, including water: | |
| --- | --- |
| | Range 1% W/W(approx.) |
| 1. Wax ingredient | |
| Beeswax - white | 0.1–0.5 |
| 2. Lubricating and moisturizing agents | |
| Carbomer - 940 | 0.1–1.0 |
| Glyceryl stearate | 1.0–4.5 |
| Isopropyl palmitate | 0.25–5.0 |
| Myristyl myristate | 2.0–5.0 |
| | 3.35–15.5 |
| 3. Emulsifying agents | |
| Sorbitan stearate | 0.1–1.0 |
| Sodium stearate | 1.0–3.5 |
| Polysorbate-61 | 0.3–3.0 |
| | 1.4–7.5 |
| 4. Buffering agent | |
| Concentrated hydrochloride acid | 0.001–0.003 |
| 5. Water | |
| Purified water | 63.0–92.5 |

The basic formula of active ingredients, including water, and having a neutral pH, may be set forth in category form as follows:

| | Range: % W/W (aporox.) |
| --- | --- |
| 1. Beeswax | 0.1–0.5 |
| 2. Lubricating and moisturizing agents | 3.35–15.5 |
| 3. Emulsifying agents | 1.4–7.5 |
| 4. Buffering agent | 0.001–0.003 |
| 5. Water | 63.0–92.5 |

For a commercial product, the following additional ingredients should be used:

| Additional Ingredients | Range: % W/W (approx.) |
| --- | --- |
| 1. Stabilizing agent | |
| Sodium oleate | 0.3–0.6 |
| 2. Viscosity control agents | |
| Cetyl alcohol | 0.1–5.0 |
| Stearyl alcohol | 0.1–2.5 |
| | 0.2–7.5 |
| 3. Skin oil solvent | |
| Propylene glycol | 2.0–5.0 |
| 4. Preservatives | |
| Methylparaben | 0.1–0.2 |
| Benzyl alcohol | 0.01–0.05 |
| BHT | 0.003–0.006 |
| Butylparaben | 0.01–0.02 |

-continued

| Additional Ingredients | Range: % W/W (approx.) |
|---|---|
| Propylparaben | 0.01–0.1 |
| | 0.133–0.376 |
| 5. Coloring agents | |
| FD&C Yellow #5 | 0.001–0.002 |
| FD&C Blue #1 | 0.001–0.01 |
| | 0.001–0.012 |

The additional ingredients may be set forth in category form as follows:

| | Range: % W/W (approx.) |
|---|---|
| 1. Stabilizing agent | 0.3–0.6 |
| 2. Viscosity control agents | 0.2–7.5 |
| 3. Skin oil solvent | 2.0–5.0 |
| 4. Preservatives | 0.133–0.376 |
| 5. Coloring agents | 0.001–0.012 |

The complete commercial formula, combining the active and additional ingredients and having a neutral pH may be set forth in category form as follows:

| | Range % W/W (approx.) |
|---|---|
| 1. Beeswax | 0.1–0.5 |
| 2. Lubricating and moisturizing agents | 3.35–15.5 |
| 3. Emulsifying agents | 1.4–7.5 |
| 4. Buffering agent | 0.001–0.003 |
| 5. Water | 63.0–92.5 |
| 6. Stabilizing agent | 0.3–0.6 |
| 7. Viscosity control agents | 0.2–7.5 |
| 8. Skin oil solvent | 2.0–5.0 |
| 9. Preservatives | 0.133–0.376 |
| 10. Coloring agents | 0.001–0.012 |

The preferred commercial formula embodying the present invention, combining both active and additional ingredients and having a neutral pH, is set forth as follows:

| | Range: % W/W |
|---|---|
| Beeswax, White | 0.1–0.5 |
| Methylparaben | 0.1–0.2 |
| Carbomer-940 | 0.1–1.0 |
| Glyceryl Stearate | 1.0–4.5 |
| Isopropyl Palmitate | 0.25–5.0 |
| Benzyl Alcohol | 0.01–0.05 |
| Cetyl Alcohol | 0.1–5.0 |
| BHT | 0.003–0.006 |
| Concentrated Hydrochloric Acid | 0.001–0.003 |
| Butylparaben | 0.01–0.02 |
| Sorbitan Stearate | 0.1–1.0 |
| Propylene Glycol | 2.0–5.0 |
| Propylparaben | 0.01–0.1 |
| Sodium Stearate | 1.0–3.5 |
| FD&C Red #40 | 0.001–0.002 |
| Myristyl Myristate | 2.0–5.0 |
| FD&C Yellow #5 | 0.001–0.002 |
| Stearyl Alcohol | 0.1–2.5 |
| Polysorbate-61 | 0.3–3.0 |
| FD&C Blue #1 | 0.001–0.01 |
| Sodium Oleate | 0.3–0.6 |
| Purified Water | 63.0–92.5 |

What is claimed is:

1. A cold-water (fresh or salt) and no-water shaving lotion, comprising the following formula measured by weight and having a neutral pH:

| | | |
|---|---|---|
| Beeswax, White, | approximately | 0.1–0.5 |
| Methylparaben | " | 0.1–0.2 |
| Carbomer-940, | " | 0.1–1.0 |
| Glycerol Stearate, | " | 1.0–4.5 |
| Isopropyl Palmitate, | " | 0.25–5.0 |
| Benzyl Alcohol | " | 0.01–0.05 |
| Cetyl Alcohol | " | 0.1–5.0 |
| BHT, | " | 0.003–0.006 |
| Concentrated Hydrochloric Acid, | " | 0.001–0.003 |
| Butylparaben, | " | 0.01–0.02 |
| Sorbitan Stearate, | " | 0.1–1.0 |
| Propylene Glycol | " | 2.0–5.0 |
| Propylparaben | " | 0.01–0.1 |
| Sodium Stearate | " | 1.0–3.5 |
| FD&C Red #40, | " | 0.001–0.002 |
| Myristyl Myristate | " | 2.0–5.0 |
| FD&C Yellow #5, | " | 0.001–0.002 |
| Stearyl Alcohol, | " | 0.1–2.5 |
| Polysorbate-61, | " | 0.3–3.0 |
| FD&C Blue #1, | " | 0.001–0.01 |
| Sodium Oleate, | " | 0.3–0.6 |
| Purified Water, | " | 63.0–92.5 |

* * * * *